(12) United States Patent
Moore et al.

(10) Patent No.: US 8,071,325 B2
(45) Date of Patent: Dec. 6, 2011

(54) FLOW CYTOMETRIC METHOD AND KIT FOR METAL-INDUCED SENSITIVITY

(75) Inventors: Jonni Moore, Moorestown, NJ (US); Milton D. Rossman, Philadelphia, PA (US); Tatyana N. Milovanova, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 393 days.

(21) Appl. No.: 10/594,620

(22) PCT Filed: Mar. 31, 2005

(86) PCT No.: PCT/US2005/010933
§ 371 (c)(1),
(2), (4) Date: Jun. 27, 2007

(87) PCT Pub. No.: WO2005/094382
PCT Pub. Date: Oct. 13, 2005

(65) Prior Publication Data
US 2007/0287168 A1   Dec. 13, 2007

Related U.S. Application Data

(60) Provisional application No. 60/558,500, filed on Apr. 1, 2004.

(51) Int. Cl.
*G01N 33/00* (2006.01)
*G01N 33/53* (2006.01)
(52) U.S. Cl. ........................ 435/7.24; 436/811
(58) Field of Classification Search .................. None
See application file for complete search history.

(56) References Cited

U.S. PATENT DOCUMENTS

2003/0228635 A1   12/2003   Hu et al.
2006/0263761 A1*  11/2006   Fontenot et al. ............ 435/4

OTHER PUBLICATIONS

McCabe et al. Low Level Lead Exposure In Vitro Stimulates the Proliferation and Expansion of Alloantigen-Reactive CD4High T-Cells; Toxicology and Applied Pharmacology, vol. 177 (2001) pp. 219-231.*
Nygaard et al. Blood and Spleen Lymphocytes As Targets for Immunotoxic Effects in the Rat—A Comparison; Toxicology, vol. 174 (2002) pp. 153-161.*
Fontenot et al. Target Organ Localization of Memory CD4+ T Cells in Patients With Chronic Beryllium Disease; The Journal of Clinical Investigation, vol. 110, No. 10 (2002) pp. 1473-1482.*
Fontenot et al. CD28 Costimulation Independence of Target Organ Versus Circulating Memory Antigen-Specific CD4+ T Cells; The Journal of Clinical Investigation, vol. 112, No. 5 (2003) pp. 776-784.*
Shapiro, H.M. Parameters and Probes; Practical Flow Cytometry, Chapter 7.12, (2003) pp. 369-381.*
Jabbour et al. A Flow Cytometric Assay for Beryllium Sensitization: Screening and Mechanistic Applications; Beryllium Research Symposium: Basic Mechanisms and Human Health, Jun. 25-25, 2002. downloaded from: http://www.ornl.gov/sci/techresources/meetings/beryllium/session1.shtml.*
Amicosante M, et al. Beryllium binding to HLA-DP molecule carrying the marker of susceptibility to berylliosis glutamate beta 69.. Hum Immunol 2001;62:686-693.
Appay V, et al. Characterization of CD4($\beta$) CTLs ex vivo. J Immunol 2002;168:5954-5958.
Barna BP et al. Clinical application fo Beryllium Lymphocyte Proliferation Testing. Clin Diagn Lab Immunol 2003;10:990-994.
Bartell SM, et al. Risk estimation and value-of-information analysis for three proposed genetic screening programs for chronic beryllium disease prevention. Risk Anal 2000;20:87-99.
Bernard S, et al. Analysis of cell kinetics using a cell division marker. Mathematical modeling of experimental data. Biophys J 2003;84:3414-3424.
Bill JR, et al. Beryllium presentation to CD4$\beta$ T cells is dependent on a single amino acid residue of the MHC class II beta-chain. J Immunol 2005;175:7029-7037.
Deubner D, et al. Beryllium sensitization, chronic beryllium disease, and exposures at a beryllium mining and extraction facility.. Appl Occup Environ Hyg 2001;16:579-592.
Deubner DC, et al. Variability, predictive value, and uses of the beryllium blood lymphocyte proliferation test (BLPT): Preliminary analysis of the ongoing workforce survey. Appl Occup Environ Hyg 2001;16:521-526.
Farris GM, et al. Detection of Beryllium sensitivity using a flow cytometric lymphocyte proliferation test: The Immuno-Be-LPT. Toxicology 2000;143:125-140.
Fontenot AP, et al. Frequency of beryllium-specific, central memory CD4$\beta$ T cells in blood determines proliferative response. J Clin Invest 2005;115:2886-2893.
Givan AL, et al. A flow cytometric method to estimate the precursor frequencies of cells proliferating in response to specific antigens.. J Immunol Methods 1999;230:99-112.
Henneberger PK, et alBeryllium sensitization and disease among long-term and short-term workers in a beryllium ceramics plant. Int Arch Occup Environ Health 2001;74:167-176.
Henneberger PK, et al. Industries in the United States with airborne beryllium exposure and estimates of the numbers of current workers potentially exposed. J Occup Environ Hyg 2004;1:648-659.
Janeway CA Jr, et al. CD4$\beta$ T cells: Specificityand function. Immunol Rev1988; 101:39-80.
Kreiss K, et al. Chronic beryllium disease—From the workplace to cellular immunology, molecular immunogenetics, and back. Clin Immunol Immunopathol 1994;71:123-129.
Kreiss K, et al. Screening blood test identifies subclinical beryllium disease. J Occup Med 1989;31:603-608.
Lehnert NM, et al. Inhibition of normal human lung fibroblast growth by beryllium.. Toxicology 2001;160:119-127.

(Continued)

*Primary Examiner* — Rebecca Prouty
*Assistant Examiner* — Paul Martin
(74) *Attorney, Agent, or Firm* — Pearl Cohen Zedek Latzer, LLP; Mark S. Cohen

(57) ABSTRACT

This invention provides methods for determining metal-induced sensitivity of a subject and kits for affecting the same. Specifically, the invention provides methods for using immune cell proliferation resulting from exposure to test metals as a method for determining metal-induced sensitivity in subjects.

7 Claims, 3 Drawing Sheets

OTHER PUBLICATIONS

Lyons AB, Hasbold J, Hodgkin PD. Flow cytometric analysis of cell division history using dilution of carboxyfluorescein diacetate succinimidyl ester, a stably integrated fluorescent probe. Methods Cell Biol 2001;63:375-398.

Lyons AB. Analysing cell division in vivo and in vitro using flow cytometric measurement of CFSE dye dilution. J Immunol Methods2000;243:147-154.

Lyons AB. Divided we stand: Tracking cell proliferation with carboxyfluorescein diacetate succinimidyl ester. Immunol Cell Biol 1999;77:509-515.

Maier LA. Beryllium health effects in the era of the beryllium lymphocyte proliferation test. Appl Occup Environ Hyg 2001;16:514-520.

Maier LA. Clinical approach to chronic beryllium disease and other non pneumoconiotic interstitial lung diseases. J Thorac Imaging 2002;17:273-284.

Maier LA. Genetic and exposure risks for chronic beryllium disease. Clin Chest Med 2002;23:827-839.

McCanlies EC, et alHLA-DPB1 and chronic beryllium disease: A HuGE review.. Am J Epidemiol 2003; 157:388-398.

Milovanova T, et al.Flow Cytometric Test for Beryllium Sensitivity. Cytometry part B Clinical Cytometry 2004;60:23-30.

Newman LS. Significance of the blood beryllium lymphocyte proliferation test. Environ Health Perspect 1996;104 (Suppl 5):953-956.

Nikolaeva N, et al. Differentiation of human alloreactive CD4β and Cd8β T cells invitro. Transplantation 2004;78:815-824.

Rossman MD, et alProliferative response of bronchoalveolar lymphocytes to beryllium. A test for chronic beryllium disease.. Ann Intern Med 1988;108:687-693.

Rossman MD. Chronic beryllium disease: Diagnosis and management. Environ Health Perspect 1996;104 (Suppl 5):945-947.

Rossman MD. Chronic beryllium disease: A hypersensitivity disorder. Appl Occup Environ Hyg 2001;16:615-618.

Saltini C, et al. Maintenance of alveolitis in patients with chronic beryllium disease by beryllium-specific helper T cells. N. Engl J Med 1989;320:1103-1109.

Sawyer RT, et al. Beryllium-induced TNF-{alpha} production by CD4β T Cells is mediated by HLA-DP.. Am J Respir Cell Mol Biol 2004;31:122-130.

Spitzer RL, et al. Quantification of agreement in psychiatric diagnosis. A new approach. Arch Gen Psychiatry 1967;17:83-87.

Stange AW, et al. Beryllium sensitization and chronic beryllium disease at a former nuclear weapons facility. Appl Occup Environ Hyg 2001;16:405-417.

Stokes RF, et al. Blood cell proliferation response to beryllium: Analysis by receiver-operating characteristics.. J Occup Med1991;33:23-28.

Viet SM, et al. Chronic beryllium disease and eryllium sensitization at Rocky Flats: A case-control study. Am Ind yg Assoc J 2000;61:244-254.

Viola A, et al. Lanzavecchia Quantitative contribution of CD4 and CD8 to T cell antigen receptor serial triggering. J Exp Med 1997;186:1775-1779.

Wang Z, et al. Beryllium sensitivity is linked to HLA-DP genotype.. Toxicology 2001;165:27-38.

Wells AD, et al. Following the fate of individual T cells throughout activation and Clonal Expansion. J Clinical Investigation 1997;100:3173-3183.

Wells AD, et al. T cell effector function and energy avoidance are quantitatively linked to cell division. J Immunol 2000;165:2432-2443.

Weston A, et al. Racial differences in prevalence of a supratypic HLA-genetic marker immaterialto pre-employment testing for susceptibility to chronic beryllium disease. Am J Ind Med 2002;41:457-465.

* cited by examiner

FLOW CYTOMETRIC METHOD AND KIT FOR METAL-INDUCED SENSITIVITY

CROSS-REFERENCE TO RELATED APPLICATIONS

This application is a National Phase Application of PCT International Application No. PCT/US05/10933, International Filing Date 31 Mar. 2005, claiming priority of U.S Provisional Patent Application, 60/558,500, filed Apr. 1, 2004, both of which are hereby incorporated by reference in their entirety.

FIELD OF INVENTION

This invention relates to methods for detecting metal-induced sensitivity and kits for effecting the same. This invention also relates to methods for detecting beryllium sensitivity, and kits for effecting the same

BACKGROUND OF THE INVENTION

Many metal ions produce immunosensitization. Some trace elements are strong immunosensitzers and acute exposure to high local concentrations, or prolonged exposure to lower concentrations of metal in the lung or in contact with the skin, initiates the immunological process and leads to acute or chronic disease. Exposures to such metals in the workplace, or in everyday life have considerable health consequences to society.

Occupations with the highest risk are those involving processes that generate particulates, such as metal production and machining. In general, the risk of disease is proportional to the intensity and duration of exposure to the sensitivity-inducing metal.

Chronic beryllium disease (CBD) is a hypersensitivity granulomatous disease that predominantly affects the lungs. Because of its unique properties, beryllium has become widely used in a variety of industrial applications, such as inertial guidance systems, turbine rotor blades, laser tubes, rocket engine liners, springs, aircraft brakes and landing gear, ball bearings, injection and blow mold tooling, electrical contacts, automotive electronics, X-ray tube windows, spark plugs, electrical components, ceramic applications, gears, aircraft engines, oil and gas industries, welding electrodes, computer electronics, and golf clubs.

Common manifestations of CBD include the insidious onset of exertional dyspnea, nonproductive cough, fatigue, arthralgias, and chest pain. Nonpulmonary organs, including the skin, liver, spleen, myocardium, kidneys, salivary glands, and bone, may also be affected. Lung function tests may demonstrate restrictive, obstructive, or mixed physiology, usually with a decreased pulmonary diffusing capacity. Chest radiographs are often normal in detecting early disease. With progression, diffuse infiltrates culminating in end-stage fibrosis typically occur.

Measurement of lymphocyte proliferative responses to beryllium using either peripheral blood cells or cells obtained by bronchoalveolar lavage (BAL) is the standard method of documenting beryllium sensitivity. Detecting beryllium sensitivity has been useful not only as part of the diagnostic criteria for chronic beryllium disease but also, cross sectional studies demonstrated that detecting beryllium sensitivity is useful for the early identification of subclinical and clinical beryllium-induced disease. Perhaps even more important, detection of beryllium sensitization has been used as a bioassay for the detection of exposure to abnormal environmental conditions.

The standard method for performing the lymphocyte proliferation assay utilizes tritiated thymidine to measure DNA synthesis. This has been termed the Beryllium Lymphocyte Proliferation Test or BeLPT. BeLPT is now required by the Department of Energy of the United States as part of the CBD prevention program.

In the United States, an estimated 800,000 workers were considered to be at risk for developing CBD in 1978. Because of the sensitivity of the BeLPT in identifying excessive exposures, the number of workers at risk for development of CBD in the United States is probably considerably more, and there may be over one million workers worldwide who are at risk. Thus, CBD represents a unique use of lymphocyte proliferation testing (blood and lavage), for diagnosis, screening and surveillance. However, the widespread use of the BeLPT has been criticized by some because of the variability of the test, despite efforts to standardize the method. The practice of having two laboratories test split blood samples from a given individual is reported to identify more cases of beryllium sensitization than would have been the case for either laboratory alone.

Since the onset of disease is insidious aid prolonged exposure may accelerate progression, there has been widespread recognition of the utility of beryllium screening tests for at-risk populations. Because the tritiated thymidine method of determining lymphocyte proliferation is complex and requires radioactive materials and analysis over several days, a reliable method allowing for fast, accurate and non-invasive diagnosis, screening and surveillance is desired.

SUMMARY OF THIE INVENTION

In one embodiment, the invention provides a method for deter-mining metal-induced sensitivity of a subject, the method comprising: staining a peripheral blood leukocyte (PBL) population obtained from a subject with an intracellular protein stain; contacting said population with an amount of a test metal-containing compound sufficient to stimulate or enhance proliferation of said population; and measuring the loss of intracellular protein staining, whereby loss of intracellular protein staining indicates prolifration and that a subject is sensitive to the test metal.

In another embodiment, the invention provides a kit for dignosing metal-induced sensitivity in a subject, the kit comprising: an agent which selectively labels intracellular proteins, an agent that selectively labels cell surface markers on a subpopulation of cells, at least one test-metal at a concentration sufficient to stimulate or enhance proliferation of a population of cells isolated from a subject with metal-induced sensitivity, and the software to analyze the results.

In one embodiment the test-metal is Beryllium, Titanium, Zirconium, Aluminum, Cobalt or Gold.

In another embodiment, the subject exhibits symptoms associated with Chronic beryllium disease, Granulomatous Lung Disease, Potroom Asthma, Sarcoidosis-Like Pathology, Noncaseating granulomas, Pulmonary fibrosis, or Hypersensitivity pneumonitis.

DETAILED DESCRIPTION OF THE INVENTION

Figure 1:
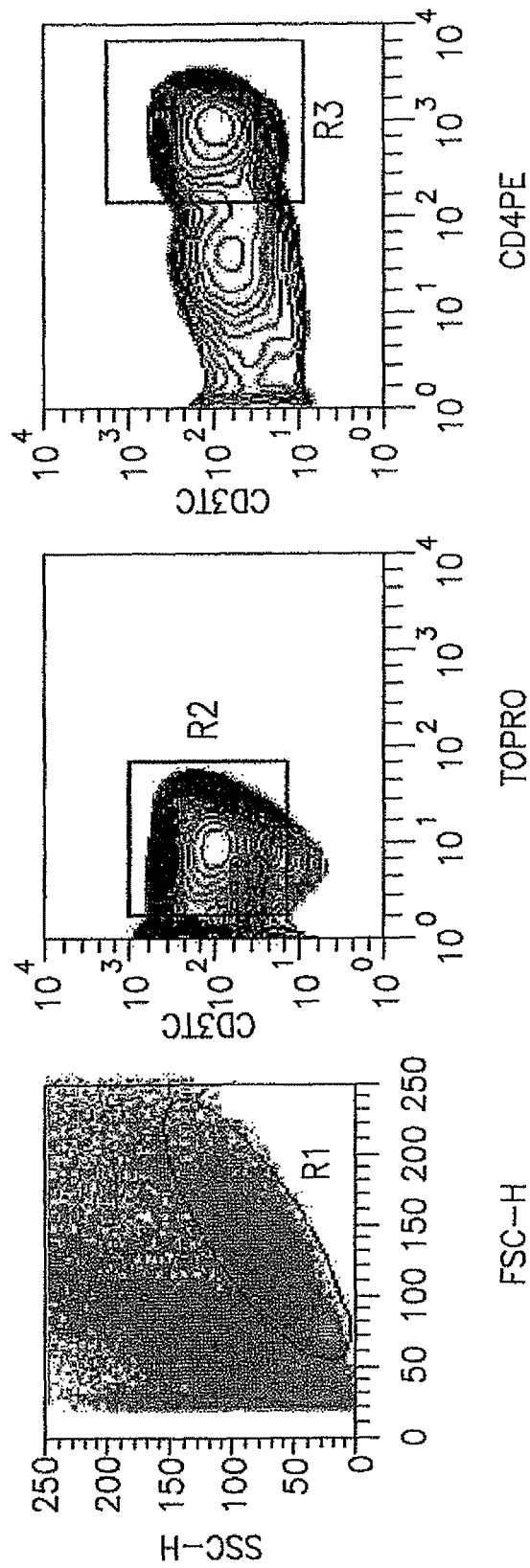
FIG 1 depict graphically the gating strategy for beryllium sensitivity analysis.

This invention provides, in some embodiments, methods for determining metal-induced sensitivity of a subject and kits for affecting the same.

In one embodiment, the invention provides a method for determining metal-induced sensitivity of a subject, the method comprising: staining a peripheral blood leukocyte (PBL) population obtained from a subject with an intracellular protein stain; contacting said population with an amount of a test metal-containing compound sufficient to stimulate or enhance proliferation of said population; and measuring the loss of intracellular protein staining, whereby loss of intracellular, protein staining indicates prolifration and that a subject is sensitive to the test metal.

In one embodiment, metal ions specifically sensitize lymphocytes, in an MHC-restricted manner. In one embodiment, immune system stimulation by metals is non-specific. In another embodiment CD4+ T-cells specifically respond as a result of metal exposure in susceptible subjects.

In one embodiment, the methods and kits of the invention are used to screen subjects for metal-induced sensitivity. In another embodiment the methods and kits are used to monitor changes in environmental conditions in the workplace. In one embodiment, the methods and kits are used to monitor potential sensitization of subject(s) in a high-risk environment. In another embodiment, the methods and kits are used to monitor effectiveness of environmental controls for removing metal dust.

In one embodiment, sensitivity refers to a state of altered reactivity in which the body reacts with an exaggerated immune response to exposure to a foreign substance. Sensitivity as used herein, encompasses in one embodiment, either immediate or delayed reactions.

Delayed sensitivity, in one embodiment, refers to an increased reactivity to specific antigens. In one embodiment, the immune response is cell mediated. In another embodiment, immediate sensitivity refers to reactions which occur within minutes of exposure to challenging antigen or metal, or in another embodiment, a sensitizing agent, due, in one embodiment, to the release of histamine, or in another embodiment smooth muscle contraction or in another embodiment increased vascular permeability. In one embodiment the reaction manifests as an allergic response, which may include in an embodiment of the invention: rash, itching, hives, swelling, difficulty breathing, and/or low blood pressure.

In one embodiment, the term "staining" or "stain" refers to the use of a label to specifically mark the indicated molecule. In one embodiment, the stain comprises an antibody or peptide, which specifically interacts or binds to the indicated molecule.

In one embodiment, a fluorochrome, luminescent compound, electron dense compound, or any other label, as will be known to one skilled in the art, serves as the label, and such label may be conjugated to the antibody or peptide, described hereinabove. In one embodiment, such a label may be referred to as "primary" in that the label is directly incorporated within the molecule providing specificity of interaction. In another embodiment, the label may be indirectly attached to the peptide or antibody, as described herein, such as, for example, a fluorochrome conjugated to an antibody which specifically recognizes another IgG molecule, with an IgG monoclonal serving as the molecule conferring specificity for labelling the cellular protein.

In one embodiment, the stain comprises an antibody. The term "antibody" is used in the broadest sense and covers, in other embodiments, monoclonal antibodies (including full length monoclonal antibodies), polyclonal antibodies, multi-specific antibodies (e.g., bispecific antibodies), antibody fragments, or combinations thereof, as will be readily appreciated by one skilled in the art.

The antibody used may be directly conjugated to a detectable label, which, in another embodiment is fluorescent. In one embodiment, antibodies are labeled via an interaction with a secondary molecule, to which the label is conjugated, as will be appreciated by one skilled in the art. In one emboidment, multiple labels may be simultaneously analyzed, for determinations of proliferation, and in one embodiment, the labels will be individually discernable, such as, for example, in the use of multiple fluorescent labels whose emission spectra do not overlap.

In one embodiment supravital fluorochromes are used to monitor leucocyte proliferation. In one embodiment staining may comprise the use of a PKH26 red fluorescent general cell linker kit (Sigma Chem. Co.). In another embodiment, the fluorochrome used is fluorescein ester which in another embodiment is a fluorescein diacetate. In one embodiment, the fluorochrome is calcein-AM (Calcein, acetoxymethyl) or in another embodiment DiI (1,1-dioctadecyl-3,3,3',3'- tetramethylindocarbocyanide perchlorate), or in another embodiment FAST-DiI (a derivative of DiI). In one embodiment BCECF-AM (2',7'-bis(carboxyethyl)-5(6')-carboxy-fluorescein-acetoxymethyl ester) is the fluorochrome used or in another embodiment CFDA (carboxyfluorescein diacetate) or in another embodiment CFSE (carboxy fluorescein diacetate succinimide ester). In one embodiment, fluorochromes such as Allophycocyanin (APC) or fluorescein are directly conjugated to the molecule conferring specificity.

In another embodiment, the method further comprises assessing viability of the cell population being evaluated. In one emboidment, cell viability is determined via the use of the vital dye TO-PRO®-3.

In one embodiment, staining may comprise staining cell surface markers. In one embodiment, cell surface markers stained may comprise CD3, CD4, CD8, or a combination thereof. In one embodiment, staining indicates absence or presence of indication, and in another embodiment, relative abundance of expression.

In one embodiment of this invention, the stains as described herein may be used in combinations in order to specifically label cell surface markers, cell membranes, intracellular or other ubiquitous proliferation markers, etc., which represents embodiments of the methods and kits of the invention.

In one embodiment, the method comprises staining cellular proteins associated with progression through the cell cycle. In one embodiment, such proteins may comprise proliferating cell nuclear antigen (PCNA), argyrophilic nucleolar organizer region (AgNOR), the proliferation-associated nuclear antigen Ki67, or combinations thereof.

In one embodiment, stains are readily taken up by the cell and are diluted as a function of cell proliferation, in the population being evaluated.

In one embodiment, staining of intracellular proteins comprises using a fixative, or a cell permeabilization agent on the cell population, for a time period and at an appropriate temperature, such as to provide greates signal, and least background for the staining. Such determinations are readily accomplished, and may employ the use of formaldehyde, paraformaldehyde, formalin, saponin, and other agents.

In one embodiment, following staining of the peripheral blood leukocyte (PBL) population, the population is contacted with an amount of a test metal-containing compound sufficient to stimulate or enhance proliferation of said population.

In one embodiment, the term "sufficient-to-stimulate" refers to a concentration or amount of metal compound, which provides immune stimulation in the subject, or in another embodiment, provides proliferation of metal-specific T-cells. In one embodiment, "sufficient-to-stimulate" refers to a concentration or amount of metal compound, which enhances immune responses in the subject, in response to even minimal exposure to the test metal. In one embodiment, enhanced immune responses are manifested by an increase in the number of cells which proliferate as a result of exposure, or in another embodiment, a detectable increase in the rate of cell division, as a result of exposure to the test metal.

As used herein, the term "proliferation" refers in one embodiment to increased multiplication of cells. In one embodiment of this invention, proliferation of T cells is specifically determined. In one embodiment, determining T cell proliferation is conducted as exemplified herein, in Example 1.

In another embodiment proliferation is measured by measuring a decrease in a concentration of a cellular label incorporated in or on a population of cells, as a function of time. In one embodiment, the label detects a protein which is ubiquitously expressed in the population. In one embodiment, proteins associated with cell cycle progression, or, in another embodiment, cell membrane stains, or in another embodiment nutrient uptake, are used to measure cell proliferation.

In one embodiment, determining cell proliferation is accomplished with the use of a fluorescent activated cell sorter (FACS).

Flow cytometry is an optical technique that analyzes particles or cells in a fluid mixture based on their optical characteristics, via the use of a flow cytometer (See, for example, Shapiro, "Practical Flow Cytometry," Third Ed. (Alan R. Liss, Inc. 1995); and Melamed et al., "Flow Cytometry and Sorting," Second Ed. (Wiley-Liss 1990)). Flow cytometers hydrodynamically focus a fluid suspension of particles/cells into a thin stream so that they flow down the stream in substantially single file and pass through an examination zone. A focused light beam, such as a laser beam illuminates the particles as they flow through the examination zone. Optical detectors within the flow cytometer measure certain characteristics of the light as it interacts with the particles/cells. Commonly used flow cytometers such as the Becton-Dickinson Immunocytometry Systems "FACSCAN" (San Jose, Calif.) can measure forward light scatter (generally correlated with the refractive index and size of the particle/cell being illuminated), side light scatter (generally correlated with the cell granularity), and particle fluorescence at one or more wavelengths.

Multiparameter cell sorting, that is the simultaneous analysis of multiple parameters, may be used as part of the methods of this invention, and such use will be known to those of skill in the art in light of the present disclosure. In one embodiment, the population of cells to be analyzed may be contacted with a panel of antibodies directed against distinct cell surface molecules, which are labeled in such a manner as to be individually distinguishable from each other, and in another embodiment, from a cell membrane labelling compound, in one embodiment, or in another, from a fluorescent label which specifically labels intracellular proteins.

For example, one may use fluorochromes that can be excited by 2 different lasers to give off light at 4 different wavelengths, with the potential, in another embodiment, for simultaneous analysis of 4 different surface antigens, or in another embodiment, 3 surface antigens, and membrane or intracellular protein labels, etc.

Subsequent cell sorting may be performed, in another embodiment, using fluorescence-activated flow cytometry, by methods well described in the art.

In one embodiment, the methods employ the use of a test metal, which, in one embodiment, is any metal capable of inducing cell proliferation, in reaction to either acute or prolonged exposure to said metal.

In one embodiment, the test metal is Beryllium, Titanium, Zirconium, Aluminum, Cobalt, Gold, Barium, Chromium, Copper, Nickel, Mercury, Platinum, Palladium, Iridium, Indium or a combination thereof.

In one embodiment, the pathophysiology of metal-sensitization comprises granuloma formation in certain tissues, including, in one embodiment, in the lung. In another embodiment, varying degrees of fibrosis are found with exposure to the test metal depending on duration and acuteness of exposure. In one embodiment, the pathologic lesions in the organs, which in one embodiment is the lung, is comprised of a cluster of immune effector cells, which are in another embodiment are lymphocytes, macrophages, epithelioid cells, multinucleated giant cells, mast cells, and fibroblasts. In one embodiment, the rim of the mature granuloma contains large numbers of mast cells that produce and release in another embodiment basic fibroblast growth factor (bFGF, FGF-2). In one embodiment, macrophages express platelet-derived growth factor and insulin-like growth factor-1, which, together with tumor necrosis factor (TNF) and other locally derived cytokines, promote in another embodiment fibroblast proliferation and secondary fibrosis. Manifestation of any of these phenomenon may signify metal-sensitivity, and subjects with the same may be screened via the methods and/or using the kits of this invention.

In one embodiment, as the cells proliferate, the signal obtained from excitation of the fluorochrome bound to the appropriate cell marker as a function of time follows a power-law kinetics described by the following equation:

$$\lambda_t = \lambda_0 \cdot e^{kt}$$

wherein $\lambda_t$ is the strength of the signal at any given time t
  $\lambda_0$ is the initial signal strength
  k is a constant that in one embodiment may be used to quantify the relative sensitizing ability of the test metal.

The term "subject" refers in one embodiment to any living organism in which a response is elicited. The term subject includes in one embodiment, humans, or in another embodiment, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and will be applicable as will be known to one skilled in the art.

In one embodiment, the subject exhibits symptoms associated with Chronic beryllium disease, Granulomatous Lung Disease, Potroom Asthma, Sarcoidosis-Like Pathology, Non-caseating granulomas, Pulmonary fibrosis, or Hypersensitivity pneumonitis.

In one embodiment, the subject exhibits symptoms associated with Asthma. Asthma is a common disease, with a high prevalence in the developed worlds. Asthma is characterized in another embodiment by increased responsiveness of the tracheobronchial tree to a variety of stimuli, wherein in another embodiment the primary physiological disturbance being reversible airflow limitation, which may in one embodiment be spontaneous or in another embodiment metal-inhalation-related, and the pathological hallmark being inflammation of the airways.

In one embodiment, the subject exhibits symptoms associated with Potroom Asthma. The most characteristic symptoms of Potroom asthma are episodic dyspnoea, chest tightness and wheezing, temporarilly related to occupational exposure. Early identification and screening of individuals susceptible to Potroom asthma is done in one embodiment with the methods and kits of the invention and are useful for this population.

In one embodiment, the symptoms are: an initial period of symptom-free exposure (a few weeks in one embodiment, to several years in another) followed by nocturnal wheezing, or in another embodiment dyspnoea, or in another embodiment cough, or in another embodiment reversible bronchoconstriction and increased bronchial reactivity, which, in one embodiment is without evidence of allergy (normal Immunoglobulin E (IgE), and negative skin-prick tests).

According to this aspect of the invention and in one embodiment, subjects exposed to alumina, aluminium trifluoride and cryolite, as well as minor amounts of metals, such as nickel, chromium, the methods and kits of the invention may be used to screen for sensitivity of these subjects.

In one embodiment, the subject exhibits symptoms associated with sarcoidosis. Sarcoidosis is a disease characterized in one embodiment by granulomatous inflammation affecting many organs of the body and especially, in another embodiment, the lungs, lymph nodes and liver. Patients with associated symptoms may be screened in one embodiment with the methods and kits of this invention.

In one embodiment, the subject exhibits symptoms associated with hypersensitivity pneumonitis (HP). In one embodiment, hypersensitivity pneumonitis (HP) refers to a diffuse interstitial granulomatous lung disease caused by an allergic response to inhaled sensitizing agents. In one embodiment, the sensitizing agent is metal.

In one embodiment HP manifests as diffuse granulomatous interstitial pneumonitis. In another embodiment lymphocyte and plasma cell infiltrates occur along airways and in thickened alveolar septa; granulomas are single, nonnecrotizing, and randomly scattered in the parenchyma without mural vascular involvement. The degree of fibrosis depends in one embodiment on the stage of the disease.

In one embodiment, the disease is in an acute form, in which episodes of fever, chills, cough, and dyspnea occur in a previously sensitized person. In another embodiment, anorexia, nausea, and vomiting are present. In another embodiment, fine-to-medium inspiratory rales may be heard on auscultation. In one embodiment a non-acute form develops insidiously with cough and dyspnea over days to weeks. In another embodiment, the form of the disease is chronic, manifesting in one embodiment through progressive exertional dyspnea, productive cough, fatigue, and weight loss over months to years.

In one embodiment, Chest x-ray reveal normal to diffuse interstitial fibrosis. In another embodiment bilateral patchy or nodular infiltrates, coarsening of bronchovascular markings, or a fine acinar pattern suggestive of pulmonary edema are seen. According to this aspect of the invention, chest x-rays may be used to ascertain symptoms associated with metal induced HP.

In one embodiment, the subject exhibits symptoms associated with Chronic Beryllium Disease (CBD). Subjects afflicted with a chronic beryllium sensitivity disease exhibit physical manifestations that include in one embodiment inflammation of the lungs (pneumonitis), or in another embodiment abrupt onsets of coughing, or in another embodiment difficulty in breathing, or in another embodiment weight loss, fatigue, shortness of breath, chest and joint pain, blood in sputum, rapid heart rate, loss of appetite, fevers and night sweats. In another embodiment, abnormal tissue forms in the lungs and lymph nodes can enlarge.

It is to be understood that any subject manifesting with one, some or varied combinations of the clinical signs as described hereinabove, may be screened for metal-induced sensitivity, using the methods and/or kits of this invention.

In one embodiment, the subject evaluated by the methods and/or using the kits of this invention is homozygous, or in another embodiment, heterozygous, for glutamate at position 69 ($Glu^{69}$) of the HLA-DP β chain.

In one embodiment, the invention provides a method for determining metal-induced sensitivity of a subject, further comprising the step of selecting a subpopulation of the peripheral blood leukocyte population using a cell surface stain.

In one embodiment, peripheral blood leukocytes (PBLs) are isolated from heparinized blood obtained from a subject, by methods well known in the art. In, one embodiment, the blood may be diluted, or, in another embodiment, red blood cells may be lysed, and a leukocyte rich suspension may be obtained, by density centrifugation using separation medium, such as, for example, sucrose gradients, or Ficoll-hypaque solutions, and in some embodiments, the solutions are commercially available. In one embodiment, PBL's are obtained from blood samples enriched for leukocytes, such as, via the obtaining of a "buffy coat", as will be readily appreciated by one skilled in the art. In another embodiment, buffy coats may be further subjected to density gradient centrifugation. In another embodiment, PBL's are obtained from blood samples, which have not undergone any leukocyte enrichment.

In one embodiment, the PBL's may be further fractionated into surface immunoglobulin-positive [Ig(+)] and surface immunoglobulin-negative [Ig(−)] sub-populations by chromatographic separation.

In one embodiment, blood samples are obtained from a subject or, in another embodiment, a pool of subjects located in high exposure environment. In another embodiment, the test sample are frozen and tested periodically as a function of the subject or subjects' exposure, thereby serving as personal standard for each individual.

In one embodiment, the method of this invention utilizes test metal, which is a beryllium salt. In one embodiment, the beryllium salt is beryllium sulfate, which, in another embodiment is at a concentration of between about 1 to about 150 µM.

In one embodiment, the Beryllium Sulfate is at a range of between about 1 to about 30 µM, or in another embodiment between about 30 to about 60 µM, or in another embodiment between about 61 to about 90 µM, or in another embodiment between about 91 to about 120 µM, or in another embodiment between about 121 to about 150 µM.

In one embodiment, the invention provides a method for determining metal-induced sensitivity of a subject further comprises comparing the values obtained after measuring the loss of intracellular protein staining, whereby loss of intracellular protein staining indicates prolifration and that a subject is sensitive to the test metal, with a standard.

In one embodiment, "compared to a standard", refers to relative changes in PBL proliferation where the standard is derived from a single individual, or in another embodiment, is derived from pooled subjects who have been exposed to the test metal, but have not developed symptoms associated with metal-induced sensitivity. In another embodiment, a standard can be derived from a single subject following about 1 to about 5 years of having been exposed to the test-metal. In one embodiment, a standard can be derived from a subject who has been exposed to the specific metal for which the subject is being evaluated, such as, for example, being obtained from a subject having been exposed to Berylium, or in another embodiment, to Aluminum, or in another embodiment to Mercury or in another embodiment to Cobalt. In another embodiment, the standard is derived from a subject who has been exposed to a test-metal different than that which the recipient has been exposed to, however, the two individuals, or pool of individuals are of a similar genetic background.

In one embodiment, the methods may be utilized to predict the sensitivity of a subject to a test-metal. In one embodiment, metal-induced sensitivity and the method for evaluating the same, or in another embodiment, the kits for carrying out the methods of the invention, may comprise any embodiment listed herein for such purposes, and is part of the invention.

In another embodiment, the invention provides a kit for dignosing metal-induced sensitivity in a subject, comprising an agent which selectively labels intracellular proteins, and at least one test-metal at a concentration sufficient to stimulate or enhance proliferation of a population of cells isolated from a subject with metal-induced sensitivity. In one embodiment, the kit further comprises an agent that selectively labels cell surface markers on a subpopulation of the cells. In another embodiment, the kit further comprises software to analyze the results.

It is to be understood that the agents included within the kits of this invention, which label intracellular proteins, and/or cell surface markers, may comprise any of the embodiments listed herein, and are to be considered as part of this invention.

In one embodiment, the kit further may comprise agents, which detect activity or in another embodiment expression of a protein product. In one embodiment the agents may comprise antibodies that detect the presence of specific nucleic acids.

In one embodiment, the kit may further comprises a positive and/or negative standard, wherein the standard can be assayed and compared to the test sample. It is to be understood that the kits of the invention may be modified and marketed for particular use.

In one embodiment, the results obtained are compared to a standard, which, in another embodiment, may comprise a series of standards, which, in another embodiment is used in the kits of the invention for quantification of differential expression. In one embodiment, the standard may comprise any embodiment listed herein, and in another embodiment, will be suitable for a particular application of the kit.

In one embodiment, the kit of the invention may further comprise a software package contained on a computer storage medium, with a program for correlating values obtained with a standard, for storing and comparing, by date, or in another embodiment for extrapolating results obtained.

In the methods and kits according to embodiments of the present invention, data relating to values obtained for the parameters for sensitized and non-sensitized samples analyzed may be provided in a database such as Microsoft Access, ORACLE, other SQL databases or simply in a data file. The database or data file may contain, for example, a patient identifier such as a name or number, the values obtained, patient prognosis, age of onset of symptoms, therapy regimen, and other identifying and relevant characteristics, as will be understood by one skilled in the art. The database may contain, in other embodiments, the change in any of the parameters analyzed, as a function of time, or treatment regimen, or a combination thereof. In one embodiment, the methods and kits of this invention may further comprise accessing a memory, or a means thereto for storing the obtained values for the parameters, and other data as described herein. In another embodiment, the methods of this invention may further comprise generating and graphically displaying the values obtained. In one embodiment, the analysis is executed by a processor or a virtual computer program.

In one embodiment the software incorporates statistical tools for determining the significance of the findings.

Statistical significance is determined, in other embodiments, by conducting pairwise comparisons, and determining a p value. See, e.g., Dowdy and Wearden, Statistics for Research, John Wiley & Sons, New York, 1983. In one embodiment, a p value of 0,1, 0.05, 0.025, 0.02, 0.01, 0.005, 0.001, 0.0001, or less is indicative of a significant difference.

The following examples are presented in order to more fully illustrate the preferred embodiments of the invention. They should in no way be construed, however, as limiting the broad scope of the invention.

EXAMPLES

Example 1

Flow Cytometry Provides a Sensitive, Non-Radioactive Test Measuring Beryllium Sensitivity with Added Specificity of Enabling Phenotypic Description of the Responding Cell Type Materials and Methods
Population Tested Beryllium workers (present and former), referred to the Hospital of the University of Pennsylvania (HUP) for possible CBD, were tested. Individuals were considered to have beryllium hypersensitivity (BH) if they had a positive blood BeLPT on at least two occasions or a positive bronchoalveolar lavage (BAL) BeLPT. CBD was diagnosed when there was evidence of BH with granulomas on biopsy and/or radiologic changes consistent with a granulomatous process. Normal unexposed volunteers were used as controls.

Blood BeLPT ($^3$H-thymidine Incorporation Assay).

Peripheral blood lymphocytes (PBLs) were isolated from heparinized blood under sterile conditions using density centrifugation with lymphocyte separation medium (ICN Biomedicals Inc., Aurora, Ohio). Blood BeLPT was performed. The cells were cultured at a concentration of $2.5 \times 10^5$ cells/well. Stimulants included 500 µg/ml of phytohemagglutinin (PHA) (L-9132; Sigma Chemical Co., St Louis, Mo.), 20 µl/ml of Candida(M15; Greer Labs, Lenoir, N.C.) and 100 µM or 10 µM of beryllium sulfate (Blush Wellman, Cleveland, OH). After culturing the cells in an incubator (5% $CO_2$ and 37° C.) for 3, 5 or 7 days, the cells were pulsed with $^3$H thymidine (DuPont NEN, Boston, Mass.) overnight (ice. 16-24 hours) and then harvested on a filter fiber (Wallac, Turku, Finland). The uptake of $^3$H thymidine was measured as counts per minute (CPM) using a Wallac 1205 beta plate liquid scintillation system (Wallac Inc., Gaithersburg, Md.). Results were expressed as a stimulation index (SI=mean CPM of test wells/mean CPM of control wells). A positive response was defined as a SI>3.0 for blood A positive test required that a positive response be recorded on two different days or at two different concentrations of beryllium.

Surface and Intracellular Staining

Cell surface marker staining was performed. The following monoclonal antibodies were used: Phycoerythin (PE) conjugated anti-human CD4, Tricolor-conjugated anti-human CD3, Allophycocyanin (APC) conjugated anti-human CD8 (Caltag, Burlingame, Calif.). The vital dye TO-PRO®-3 (Molecular Probes Inc., Eugene, Oreg.) was used to discriminate live and dead cells.

For intracellular staining, cells were fixed for 20 minutes with 2% formaldehyde at room temperature. After two washes in 0.5% BSA, cells were then permeabilized with 0.1% saponin (Sigma Chemical Co., St. Louis, Mo.) in PBS containing 0.5% BSA for ten minutes at room temperature. Intracellular staining was performed for 30 minutes with cells resuspended in a small volume of 0.1% saponin in 0.5% BSA at room temperature. After two washes in a 0.1% saponin, the cells were resuspended in PBS with 0.5% BSA and analyzed by flow cytometry.

CFSE Labeling and Measurement of Proliferation.

The CFSE labeling method was adapted from a previously described protocol. Aliquots of the same PBL sample used in the BeLPT assay were split and washed three times in 10 ml of phosphate buffered saline (dPBS, Gibco BRL, Grand Island, N.Y.) at room temperature. The cells were adjusted to $10^6$ cells per milliliter, and CFSE (Molecular Probes, Eugene, Oreg.) was added at a final concentration of 1 µM/ml. The cells were vortexed for ten seconds and then incubated for ten minutes in the dark at room temperature with gentle shaking. After incubation an equal volume of sterile, heat inactivated human serum (Gibco BRL, Grand Island, N.Y.) was added to the sample for one minute to quench the reaction. The cells were washed twice, adjusted to the concentration $2 \times 10^6$/ml in 10% human heat inactivated serum.

Following CFSE (carboxy fluorescein diacetate succinimide ester) labeling, the cells were cultured in 24-well plates at $2 \times 10^6$ per well in the presence of either media alone, PHA, Candida, or either 10 or 100 µM of beryllium sulfate. The cells were incubated for seven days at 37° C. and 5% $CO_2$. Preliminary experiments titrated the optimal dose of CFSE and time of incubation. Surface labeling was performed at the time of harvest using CD3TC, CD4PE and CD8APC in some experiments. TO-PRO®-3 was added to define live cells in some experiments.

Flow Cytometric Data Acquisition and Analysis.

All data were acquired on a four-color, dual laser FACSCalibur (Becton Dickinson, San Jose, Calif.). CFSE was measured in Fl-1 channel (530/30-nm bandpass filter), CD4PE in the Fl-2 channel (585/42-nm bandpass filter), CD3TC in the Fl-3-channel (670-nm longpass filter) using excitation from the 488 nm blue laser and TO-PRO®-3 or CD8APC in Fl-4 channel (661/16 bandpass filter) by excitation using the 635 nm red diode laser. Compensation for CFSE in multiparameter flow cytometry is dose dependent and determined empirically.

The basic analysis gating strategy was as follows (FIG. 1): for analysis of CD3+ T cells alone, an initial region was defined as lymphocytes by light scatter and a broad region was set to include medium to high forward/low side scatter events after stimulation with PHA (FIG. 1A, R1) to include all proliferating lymphocytes. For CD3+ T cells, the R1 data were plotted in a contour plot of CD3TC versus TO-PRO®-3 to identify the live CD3+ T Cells (FIG. 1B, R2). The R2 population was expressed on a contour plot of CD3+CD4+ where a double positive region was defined as R3 (FIG. 1C).

For final analyses, each population was then analyzed for CFSE (FL1) fluorescence, representing proliferation, on a single parameter histogram using a logical gate of either R1*R2 for CD3+ cells only and R1*R2*R3 for CD3+4+ cells. In experiments where only data from CD3+ or CD3+4+ cells were collected, a live gate on TO-PRO®-3 negative ("viable") cells was also used in acquisition. When specific CD4+ and CD8+ T cell determination was performed, the viability dye was eliminated. The strategy was similar to that above with light scatter gating (R1) followed by identification of the CD3+ events using a SSC vs CD3+ plot (R2) and CD4+ (R3) and CD8+(R4) identification followed by single parameter histogram analysis of the CFSE fluorescence (for CD4+, R1*R2*R3; for CD8, R1*R2*R4*).

CFSE flow cytometric data files were analyzed using CellQuest™ acquisition/analysis software (Becton Dickinson, San Jose, Calif.). Fifty thousand (50,000) events were collected. The data are reported as the proliferative ratio (PR) defined as the ratio of the percentage of divided cells to undivided cells on day 7 (%M2/%M1). The metric of percent dividing cells is used for comparing flow cytometry measures of proliferation to standard $^3$H thymidine methods.

Statistical Analysis

All values are presented as ± SEM (standard error of the mean). Data are only presented if a minimum of 1,000 cells were detected within a population. For the tritiated thymidine test, the results were expressed as a stimulation index and group differences (between controls and beryllium-sensitive populations) were evaluated using the Student's T test. For the CFSE tests, since the results were expressed as PR, the Mann-Whitney version of the Wilcoxon Signed Rank test was used to determine if there was a difference between the normal donors and the beryllium exposed patients. Statistical significance was defined as p<0.05.

Results

Beryllium Sensitivity Measured by Thymidine Incorporation

Nine normal unexposed controls and 24 beryllium-exposed individuals previously shown to be sensitized to beryllium were analyzed in the first series of experiments. Four of the 24 were diagnosed with CBD based on the positive blood and previous bronchoalveolar lavage (BAL) BeLPT and had granulomas on biopsy; seven of 24 had a diagnosis of beryllium alveolitis, based on findings of positive blood and BAL BeLPT without granulomas on biopsy; and 13 had a diagnosis of beryllium hypersensitivity based on positive blood BeLPT on at least two occasions with negative findings on bronchoscopy. Positive responses were observed in the control and beryllium-sensitized populations for the response to PHA on day 3 and Candida on day 5 and on day 7 (Table 1). There were no significant differences in these responses between these two groups. In contrast, while positive responses to beryllium were not noted in the control group, positive responses were noted to beryllium in the beryllium-sensitized population (p<0.05).

TABLE 1

Mitogen and antigen-induced proliferative responses of cells from control and beryllium-sensitized subjects measured by thymidine incorporation.

| | Subject Groups | |
|---|---|---|
| Stimulants | Normal controls (n = 9) | Beryllium-exposed sensitized (n = 24) |
| Day 3 | | |
| Unstimulated (CPM) | 571 ± 72.5* | 598 ± 77.5 |
| PHA (SI) | 137 ± 38.9† | 178 ± 23.2 |
| Day 5 | | |

TABLE 1-continued

Mitogen and antigen-induced proliferative responses of cells from control and beryllium-sensitized subjects measured by thymidine incorporation.

| | Subject Groups | |
|---|---|---|
| Stimulants | Normal controls (n = 9) | Beryllium-exposed sensitized (n = 24) |
| Unstimulated (CPM) | 827 ± 215 | 988 ± 254 |
| Candida (SI) | 13.5 ± 3.3 | 30.3 ± 9.14 |
| Be 10 μM (SI) | 0.72 ± 0.08 | 12.1 ± 3.96‡ |
| Be 100 μM (SI) | 0.74 ± 0.09 | 12.8 ± 4.93‡ |
| Day 7 | | |
| Unstimulated (CPM) | 1,750 ± 596* | 2,710 ± 872* |
| Candida (SI) | 24.3 ± 8.1 | 29.2 ± 8.07 |
| Be 10 μM (SI) | 0.44 ± 0.08 | 12.5 ± 4.43‡ |
| Be 100 μM (SI) | 0.52 ± 0.12 | 11.5 ± 4.86‡ |

*values represent mean ± SEM of the CPM
†values represent mean ± SEM of the SI
‡= $p < 0.05$ (compared to controls)

CFSE-measured CD3+/CD4+ T Cell Response to Beryllium in vitro

To verify that detection of cell proliferation by flow cytometry is possible, CFSE-labeled peripheral blood mononuclear cells were cultured for seven days in the presence of culture media alone, PHA, Candida, 10 or 100 μM beryllium sulfate. After seven days of culture, cells were harvested and surface stained with CD3TC/CD4PE/TO-PRO®-3. PHA and Candida were used as positive controls because of their strong T cell stimulation effect. For negative controls, unstimulated cells labeled with CFSE were used. A live gate was used (TO-PRO®-3) to exclude any dead cells that might have lost CFSE.

Figure 2:
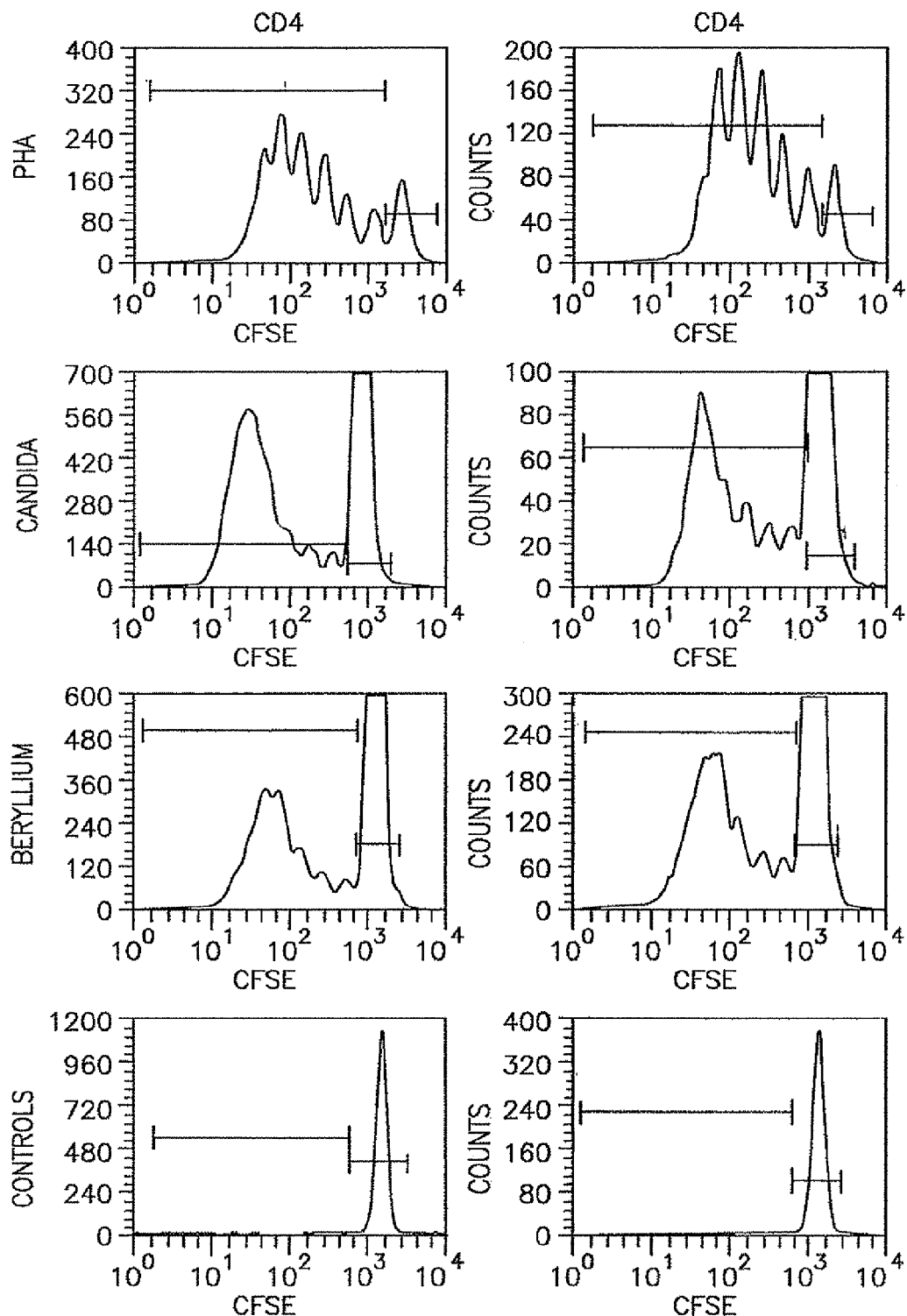
FIG. 2 is a graph showing example of CFSE-labeled CD3+, CD4+ T cell proliferation cultured for seven days with PHA, Candida, 100 μM BeSO$_4$ or control.

In the initial series of experiments, the live CD3+ cell population (TO-PRO®-3 negative) that were CD4+ high (positive) were gated on and the proportion of cells that had divided (PR) from the histograms was calculated. Flow cytometric analysis of CFSE-labeled lymphocytes revealed a typical pattern of proliferating cells detectable in both the mitogen and beryllium treated cultures demonstrating that the response to beryllium is detectable. Control cultures (unstimulated) exhibited no loss of CFSE intensity (FIG. 2, Table 2).

TABLE 2

Mitogen and antigen CD3+ and CD3+/CD4+ T-lymphocytes responses from beryllium-sensitized subjects and beryllium-unexposed donor controls measured by CFSE dye dilution.

| Subset/ treatments | Normal controls (n = 9) | Beryllium-exposed sensitized (n = 24) |
|---|---|---|
| Stimulants | CD3+ | CD3+ |
| Unstimulated | 0.023 ± 0.005† | 0.037 ± 0.004 |
| PHA | 9.853 ± 2.908 | 10.358 ± 4.730 |
| Candida | 0.105 ± 0.041 | 0.396 ± 0.254 |
| Be 10 μM | 0.027 ± 0.005 | 0.115 ± 0.046‡ |
| Be 100 μM | 0.030 ± 0.008 | 0.099 ± 0.026 |
| | CD3+/CD4+ | CD3+/CD4+ |
| Unstimulated | 0.023 ± 0.005 | 0.036 ± 0.005 |
| PHA | 10.064 ± 2.753 | 15.756 ± 5.094 |
| Candida | 0.076 ± 0.035 | 0.114 ± 0.020 |
| Be 10 μM | 0.027 ± 0.005 | 0.105 ± 0.038‡ |
| Be 100 μM | 0.029 ± 0.010 | 0.089 ± 0.027‡ |

†values represent mean +/− SEM of the PR
‡= $p < 0.05$ (compared to controls)

Similar to the results with tritiated thymidine, positive responses to PHA and Candida were noted for the CD3+, and CD3+CD4+ cells from both the control and the beryllium-sensitive populations (Table 2). There was minimal response detected in the CD3+, or CD3+/CD4+ high cells from controls to 10 or 100 μM $BeSO_4$. In contrast, the cells from the beryllium-sensitive population had a significant positive response to 10 μM $BeSO_4$ in the CD3+ population and to 10 μM and 100 μM $BeSO_4$ in the CD3+/CD4+ population ($p<0.05$). As expected, no significant differences were noted between the cells from normals and the cells from the subjects with beryllium sensitivity in the CFSE-determined response to PHA or Candida. When the values from beryllium sensitized patients were compared to those obtained from normal controls, it was determined that the CFSE method could discriminate between these two groups. Of note, in some experiments, there appeared to be a positive beryllium response in the CD3+/CD4+ low population.

CFSE-measured Proliferative Response of CD4+ and CD8+ T Cells to Beryllium in vitro In the initial experiments, it was not possible to determine the exact phenotype of the CD3+/CD4 low cells, although in many cases they may represent CD8+ T cells. Finding a beryllium response in a population of possible CD8+ T cells was unexpected since there is not thought to be a CD8+ response to beryllium in vitro. However, in cultured T cells, CD3+ high/CD4+ low T cells may contain not only CD8+ T cells but also CD4+ T cells with surface CD4 that has been down regulated. Since in the first series of experiments, gating on live cells, using TO-PRO®-3, was observed not to offer significant advantage over light scatter gating for viability, therefore, TO-PRO-3 was replaced with anti-CD8+ APC. By using this four-color flow cytometry staining technique, we could measure the proliferation of CD3+/CD4+ and CD3+/CD8+ cell populations.

CD3+, CD3+/CD4+ and CD3+/CD8+ T cells from controls (n=6) and beryllium-sensitized (n=14) populations responded to both PHA and Candida in vitro as. In contrast, while a significant difference in the response of the CD3+ and CD3+/CD4+ T cells from beryllium-sensitized subjects was detected to both doses of $BeSO_4$, no differences were noted in the response of CD8+ T cells from either normal donors or beryllium-sensitized individuals consistent with previous reports (Table 3).

TABLE 3

Beryllium responses of CD3+, and CD3+/CD4+ and CD3+/CD8+ subpopulations from control and beryllium-sensitized subjects as measured by CFSE dye dilution.

| Subsets/ treatments | Normal controls (n = 6) | Beryllium-exposed sensitized (n = 14) |
|---|---|---|
| | CD3+ | |
| Be 10 μM | 0.012 +/− 0.002† | 0.156 +/− 0.114‡ |
| Be 100 μM | 0.013 +/− 0.002 | 0.188 +/− 0.137‡ |
| | CD4+ | |
| Be 10 μM | 0.015 +/− 0.003 | 0.164 +/− 0.112‡ |
| Be 100 μM | 0.015 +/− 0.002 | 0.210 +/− 0.114‡ |
| CD8+ | (n = 4) | (n = 11) |
| Be 10 μM | 0.013 +/− 0.003 | 0.016 +/− 0.003 |
| Be 100 μM | 0.011 +/− 0.004 | 0.019 +/− 0.002 |

†values represent mean +/− SEM of the PR
‡= $p < 0.05$ (compared to controls)

Figure 3A:
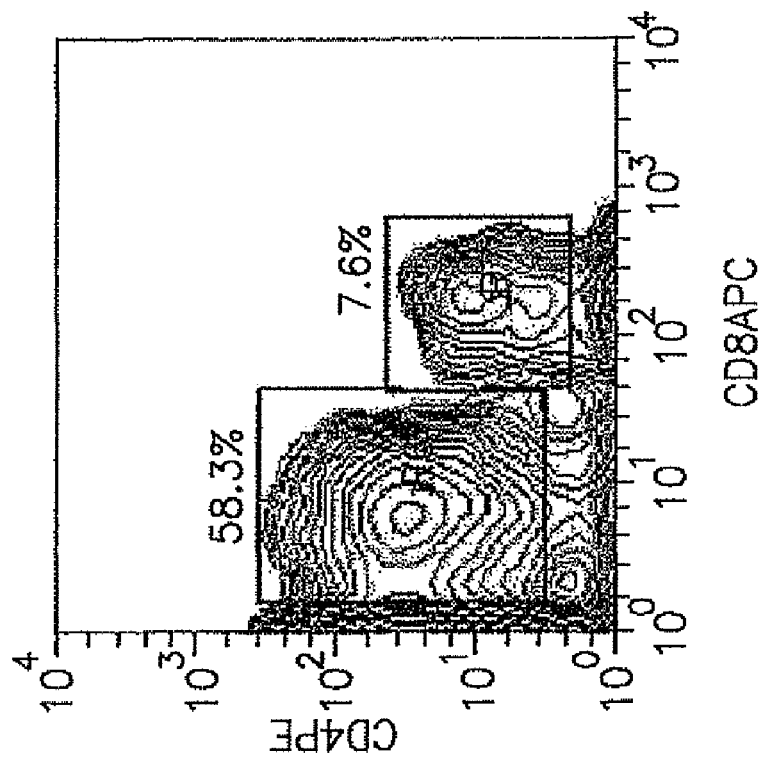
FIG. 3A-3B show contour plots of cells of an individual with a positive BeLPT.
Figure 3B:
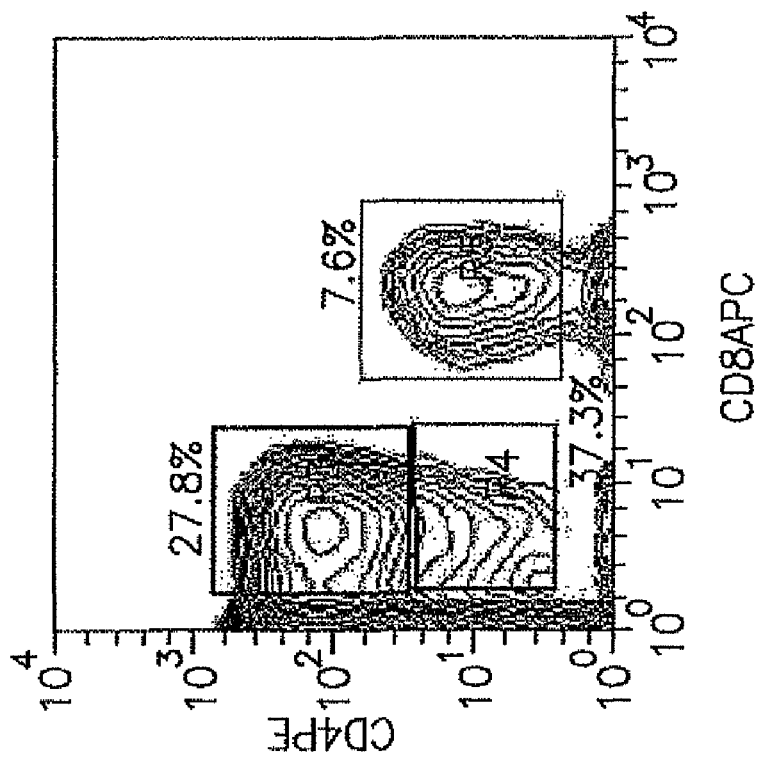

To further confirm that the "CD4+ low" response was indeed due to CD4+ cells that may have lost surface expression of this marker, intracellular staining with anti-CD4 was performed to confirm the identity of the cells. T cells from a beryllium-sensitive individual were labeled with CFSE and cultured for seven days in the presence of 10 or 100 μM beryllium sulfate. The cells were harvested, half of the cells were surface stained with anti-CD4PE/CD8APC and the rest of the cells were permeabilized before staining. In the representative example shown here, we identified by gating on CD3+ T cells, two populations of CD4+ cells (FIG. 3). The CD4+ high population was 27.8% and the CD4+ low population was 37.3% of the T cell population. However, with intracellular staining, a more homogeneous population of CD4+ CD8− negative cells was observed (58.3%). This suggests that the CD4+ low population was the result of down regulation of surface CD4+ of a proliferated CD4+ population. Surface and intracellular staining results of anti CD8+ were identical at 7.6%.

What is claimed is:

1. A method for determining beryllium sensitivity of a subject, said method comprising:
    a. Obtaining a blood sample from a subject;
    b. Selecting a peripheral blood leukocyte (PBL) population from said blood sample;
    c. Staining said peripheral blood leukocyte (PBL) population obtained from said blood sample with an intracellular protein stain;
    d. Contacting said population with an amount of a beryllium containing compound sufficient to stimulate or enhance proliferation of said population; and
    e. Measuring the loss of intracellular protein staining, whereby loss of intracellular protein staining indicates proliferation and that a subject is sensitive to beryllium;
    wherein the method further comprises the step of selecting a subpopulation of said peripheral blood leukocyte population using a cell surface marker and a viability marker, wherein said surface marker is CD3 and wherein said viability marker enables the exclusion of dead cells that lose the intracellular protein stain.

2. The method of claim 1, wherein said subject exhibits symptoms associated with Chronic beryllium disease.

3. The method of claim 1, wherein said surface marker comprises a fluorescent agent.

4. The method of claim 1, wherein said beryllium containing compound comprises a beryllium salt.

5. The method of claim 4, wherein said beryllium salt is beryllium sulfate, at a concentration of between about 1 to about 150 μM.

6. The method of claim 1, wherein said method further comprises comparing the values obtained in step (c) with a standard.

7. The method of claim 1, wherein said viability marker is TO-PRO-3.

* * * * *